(12) United States Patent
Zhang et al.

(10) Patent No.: US 6,935,779 B2
(45) Date of Patent: Aug. 30, 2005

(54) METHOD AND APPARATUS FOR ALIGNING AN X-RAY SOURCE AND DETECTOR AT VARIOUS SOURCE TO IMAGE DISTANCES

(75) Inventors: John Jun Zhang, Waukesha, WI (US); Xianfeng Ni, Waukesha, WI (US); Eric Nicholas Stepanovich, Pewaukee, WI (US); Renuka Uppaluri, Pewaukee, WI (US); Manfred David Boehm, Waukesha, WI (US)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 275 days.

(21) Appl. No.: 10/307,131

(22) Filed: Nov. 29, 2002

(65) Prior Publication Data

US 2004/0105526 A1 Jun. 3, 2004

(51) Int. Cl.[7] ................................. G01D 18/00
(52) U.S. Cl. ................. 378/207; 378/205; 378/196
(58) Field of Search .................... 378/205, 207, 378/206, 196, 197, 163, 164; 356/399

(56) References Cited

U.S. PATENT DOCUMENTS 5,982,848 A * 11/1999 Friedrich et al. ............. 378/96

* cited by examiner

Primary Examiner—Edward J. Glick
Assistant Examiner—Irakli Kiknadze
(74) Attorney, Agent, or Firm—Quarles & Brady LLP

(57) ABSTRACT

A digital radiographic imaging system includes an offset table for determining mechanical and structural offsets which would, if not corrected, misalign the source and detector during use. The method can correct for inaccuracies in mechanical linkages, examination rooms and other mounting structures, and "drift" induced during use of the system.

20 Claims, 6 Drawing Sheets

METHOD AND APPARATUS FOR ALIGNING AN X-RAY SOURCE AND DETECTOR AT VARIOUS SOURCE TO IMAGE DISTANCES

FIELD OF THE INVENTION

The present invention relates generally to digital imaging systems and, more particularly, to a system and setup procedure for determining an offset for centering a radiation source with respect to a digital detector in a digital imaging system, irrespective of variations in the dimensions of the examination room, mounting structure, or mechanical linkages.

BACKGROUND OF THE INVENTION

X-Ray systems, such as digital radiographic imaging systems, comprise an x-ray tube or source and a detector. The source is moveably mounted to a mounting structure such as a wall or ceiling in an examination room, and the detector is provided on a horizontal table or vertical stand. Typically, the detector mounting structures are also moveable in at least one direction.

In a typical setup, the source is mounted to a rail provided on the ceiling the X-ray room, and the detector or digital wall stand is provided on a stand positioned against a wall of the room. The source is moveable in longitudinal, latitudinal, and vertical directions, and may also be rotationally moved to a number of angular positions. The detector can also be moveable, typically in a latitudinal and vertical direction. Due to the large variety of possible positions, the medical imaging system is calibrated on start up such that, based on feedback, it can be determined that the source is directed at a lateral and vertical center of the detector at a known source to image distance (SID).

The installation and setup procedure for typical prior art digital imaging systems, such as digital radiographic imaging systems, are both complex and time-consuming. To comply with customer image quality and consistency requirements and various regulatory and safety standards, typical procedures require the determination of a variety of constants including fixed setpoints for laterally centering the x-ray source with respect to the center of the detector and the establishment of fixed setpoints (or detent positions) for setting the separation distance between the x-ray source and x-ray detector and calibrating the system such that an accurate readout of the separation distance can be obtained. The determination and establishment of this separation distance, referred to as the source-to-image distance (SID), assists in appropriately controlling the size of the x-ray field during diagnostic use of the imaging system. Further, many regulatory requirements specify that the SID must be clearly displayed to the operator or user of the system with a certain level of accuracy.

More recently, automated methods for establishing lateral and vertical center points of the detector have been developed. These provide an improvement over prior art methods by eliminating the need for a number of "hard" stops and detent locations, instead providing flexibility in moving the source with respect to the detector.

While each of these method of calibration are perfectly acceptable if the mechanical linkages and the mounting locations are straight, there are often irregularities in each. Therefore, as the source is moved from a calibrated position to a non-calibrated position, an offset can be induced between the expected position, and the actual position of the device. For example, in an examination room, the relative distance between the floor and the ceiling may differ across the room. Therefore, when either the X-ray source or detector is moved even in what appears to be a straight line, the source can become misaligned with the detector, resulting in an image in which the field of view is not appropriately positioned on the patient. In this case, the resultant images can be inaccurately placed or cropped, such that the portion of the anatomy sought to be imaged can be lost.

Thus, it would be desirable to provide a system for installing and calibrating a digital radiographic or other imaging system which would account for variations in the surrounding room structure when the source and detector components of the system are repositioned.

SUMMARY OF THE INVENTION

The present invention addresses one or more of the shortcomings noted above. For example, a method for calibrating the alignment of a source to a detector in a medical imaging system to account for variations due to mechanical or physical misalignments in the system includes initially determining a home position for each of the source and the detector at a known source to image distance. Thereafter, the source is moved to a second source to image distance. At the second source to image distance, and offset is calculated between an expected location of the source and an actual location of the source. During operation of the medical imaging system, the source is moved by a distance equivalent to the offset, wherein the source and detector are aligned. In another aspect, a method for calibrating the position of a digital radiographic imaging system is provided. In this method, a home position at a first known source to image distance is initially calibrated. The source to image distance is then changed, the source is directed at the detector, the source is moved to an aligned position wherein the source is aligned with the detector. An offset is calculated as a function of the aligned position. The offset is stored, and the procedure is repeated at a number of offset locations, wherein a map of offsets is developed. During real time operation, these offsets can be used to align the source and detector to prevent cropping or misalignment.

DETAILED DESCRIPTION OF THE INVENTION

The following detailed description is made with reference to a digital radiographic imaging system having an x-ray source and a digital detector configured to detect x-ray beams generated by the source. It should be understood, however, that the system and method described hereafter can be implemented in other types of digital imaging systems which have a source that generates radiation other than in the x-ray spectrum (e.g., visible light, infrared, etc.). In such imaging systems, an appropriate digital detector is provided which is configured to detect the particular type of radiation generated by the radiation source.

Figure 1:
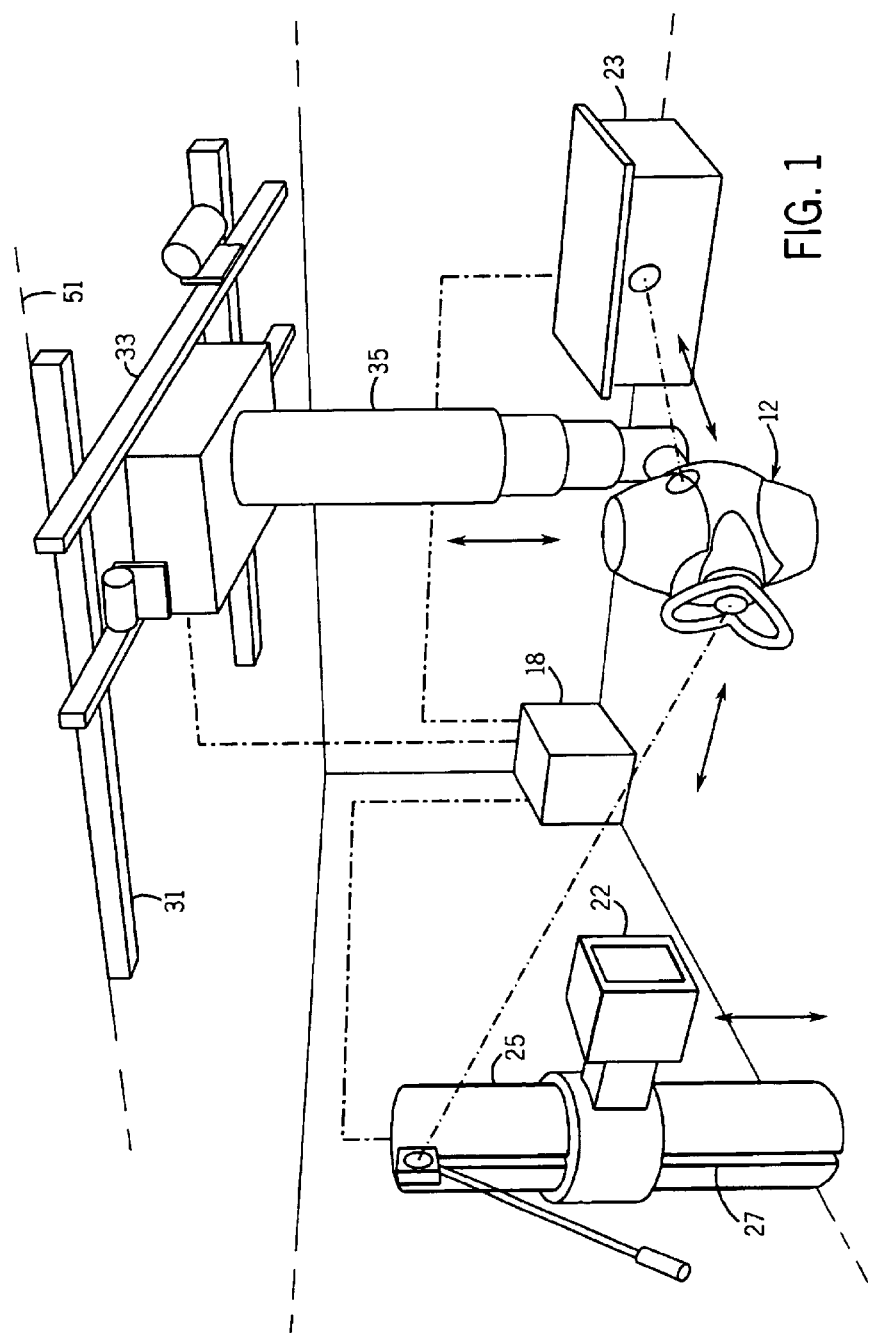
FIG. 1 is a perspective view of a digital x-ray imaging system in which the present technique is incorporated.
Figure 2:
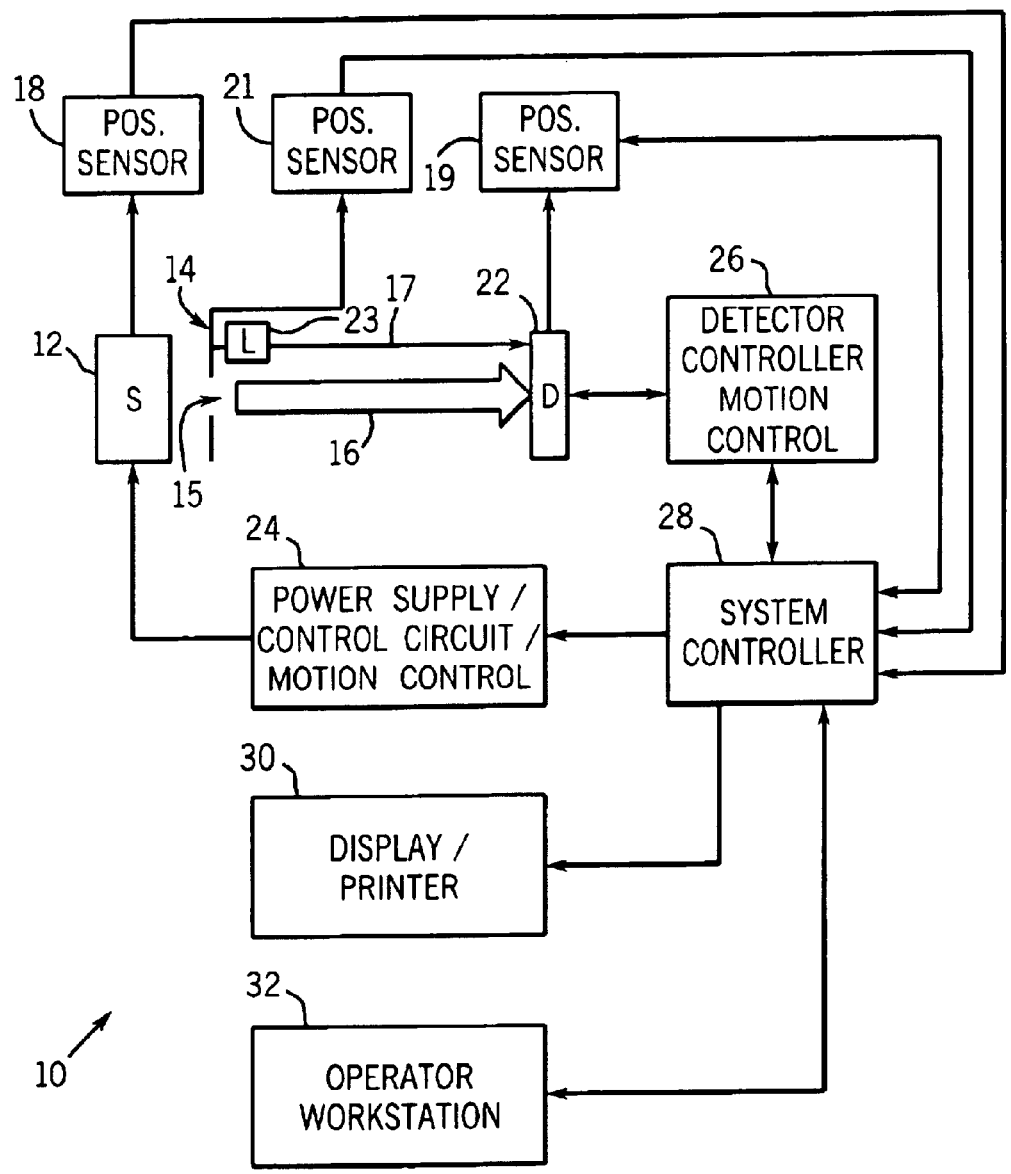
FIG. 2 is a diagrammatical overview of a digital x-ray imaging system in which the present technique is incorporated.

Turning now to the figures and more particularly to FIGS. 1 and 2, a perspective view and a diagrammatical view of an imaging system 10 for acquiring and processing discrete pixel image data is shown. In the illustrated embodiments, system 10 is a digital x-ray system that facilitates installation and calibration procedures such that accurate image data can subsequently be acquired and processed by system 10 for output and display. In the embodiment illustrated in FIGS. 1 and 2, imaging system 10 includes a source of x-ray radiation 12 having a collimator assembly 14. Source 12 is configured to generate an x-ray beam, referenced generally by the numeral 16, that passes through an opening 15 in collimator assembly 14. Opening 15 in collimator 14 is adjustable (e.g., by adjusting the position of collimator blades (not shown)) such that the size (i.e., the beam angle) of x-ray beam 16 may be varied. After passing through opening 15 in collimator assembly 14, x-ray beam 16 impacts upon and is detected by a digital x-ray detector 22. Detector 22 converts the x-ray photons received on its surface to lower energy photons, and subsequently to electrical signals which are acquired and processed to reconstruct an image. A laser 23 for directing a laser beam 17 along the trajectory of the x-ray beam 16 through the collimator 14 is included as part of the collimator assembly, and is useful in assisting in positioning and calibrating the detector 22 with respect to the source 12, as described below.

The system 10 is located in an examination room. The examination room may include, for example, a horizontal patient positioner 23 or table for positioning a subject, such as a patient, to be imaged. The horizontal positioner 23 may include a track disposed along a translational axis (e.g. the longitudinal axis) of the table for moving a detector 22 from one end of the table to another. Movement of detector 22 adds flexibility to system 10, because a movable detector allows various anatomical parts of a patient to be imaged without requiring repositioning of the patient and more easily accommodates patients of various sizes.

The examination room may also include an upright, or vertical, positioner or wall stand 25 against which a subject, such as a patient, may be positioned. Such an upright positioner 25 may include a track 27 disposed along a translational axis of the positioner 25 such that a detector 22 may be moved between upper and lower vertical positions. Again, such movement advantageously allows accommodation of subjects of different sizes and/or facilitates imaging of different anatomical targets.

The examination room further includes an x-ray source 12 which is movable in longitudinal, lateral, and vertical directions (as well as about two angular degrees of freedom), such that the source 12 can be positioned to generate an x-ray field that may be detected by a detector 22 associated with a horizontal patient positioner or a detector 22 associated with a vertical positioner 25. For example, the source 12 may be movable in the longitudinal direction along a track 31 and in a latitudinal direction along a track 33 mounted to the ceiling 51 of the examination room or the superstructure which supports the source 12, and further vertically along a telescoping arm 35. The source 12 may be movable longitudinally, laterally with respect to the longitudinal direction, and vertically with respect to the longitudinal direction. Further, the source 12 may be arranged to angularly rotate such that the same source may be used in conjunction with either a detector 22 associated with a horizontal positioner 23 or a detector 22 associated with an upright positioner 25.

In the embodiment illustrated in FIGS. 1 and 2, imaging system 10 further includes a source position sensor 18 to provide an electrical signal or electrical signals representative of the position of the source 12 in the longitudinal, lateral, and/or vertical directions, wherein the location of the source 12 can be determined in three Cartesian coordinates. System 10 further includes a detector position sensor 19 to detect the position of the detector 22 with respect to the translational axis of the horizontal positioner 23 or of the upright positioner 25. Depending on the configuration of the positioner used with the detector 22 and the corresponding number of degrees of freedom of motion, the position sensor 19 can provide an electrical signal or signals representative of the position of the detector in a longitudinal, latitudinal, vertical, rotational, and/or angular positions. For example, an upright positioner 25 is typically moveably in a vertical and angular direction, and therefore the position of the positioner 25 can be characterized with two electrical signals. Other forms of positioners can have additional axes in which motion is possible. Although the position sensors 18 and 19 are shown as a single box, the actual number of position sensors used in any given embodiment will vary depending on the number of axes in which motion is provided. Exemplary position sensors 18 and 19 are continuous position sensors, such as optical encoders, potentiometers, etc. Further, system 10 may include a position sensing transducer 21 to sense the size, or a change in the size, of opening 15 of collimator assembly 14. In an exemplary embodiment, such a position sensing transducer 21, which typically is provided in conventional collimator assemblies, may sense the size of opening 15 by sensing the position of movable collimator blades, which can be adjusted to create openings of different sizes.

Source 12 is controlled by a power supply/control circuit 24 which provides both power and control signals for installation and setup procedures, as well as for examination sequences. In an exemplary embodiment, control circuit 24 may further include positioning or motion control elements, such as motor drive circuitry and a motor, to position the source 12 along any of the longitudinal, lateral, and vertical axes. As further illustrated in FIG. 1, detector 22 is coupled to a detector controller 26, which commands acquisition of the imaging signals generated in the detector. Detector controller 26 may also execute various signal processing and filtration functions, such as for initial adjustment of dynamic ranges, interleaving of digital image data, and so forth. Detector controller 26 may also include positioning or motion control elements, such as motor drive circuitry and a motor, for positioning the detector 22 along the translational axis of the patient positioner.

Both power supply/control circuit 24 and detector controller 26 are responsive to signals from a system controller 28. In general, system controller 28 commands operation of the imaging system to execute installation and set up procedures, including generation of command signals to control movement and positioning of source 12 and detector 22. System controller 28 also commands operation of the imaging system to execute examination protocols and to process acquired image data. In the present context, system controller 28 includes signal processing circuitry, typically based upon a general purpose or application-specific digital computer, associated memory circuitry for storing programs and routines executed by the computer, as well as configuration parameters and image data, interface circuits, and so forth. In the embodiment illustrated in FIG. 2, system controller 28 (or any suitable processing module), in accordance with a stored setup program, receives feedback signals from position sensors 18, 19, and 21 and image data from detector controller 26, and processes the signals and data to determine the position of the source 12 with respect to the detector 22 and, further, to calculate and store offsets caused by irregularities in the examination room or mechanical misalignment, as described below.

In the embodiment illustrated in FIG. 1, system controller 28 is also linked to at least one output device, such as a display or printer, as indicated at reference numeral 30. The output device may include standard or special purpose computer monitors and associated processing circuitry. One or more operator workstations 32 may be further lined in the system for outputting system parameters, controlling installation and setup procedures, requesting and controlling the setup of examinations, viewing images, and so forth. In general, displays, printers, workstations, and similar devices supplied within the system may be local to the data acquisition components, such as located physically within the examination room, or may be remote from these components, such as elsewhere within an institution or hospital, or in an entirely different location, linked to the image acquisition system via one or more configurable networks, such as the Internet, virtual private networks, and so forth. In an exemplary embodiment, the operator workstation include an internet or web-based user interface which can be used in a computer processor, as described below.

Figure 3:
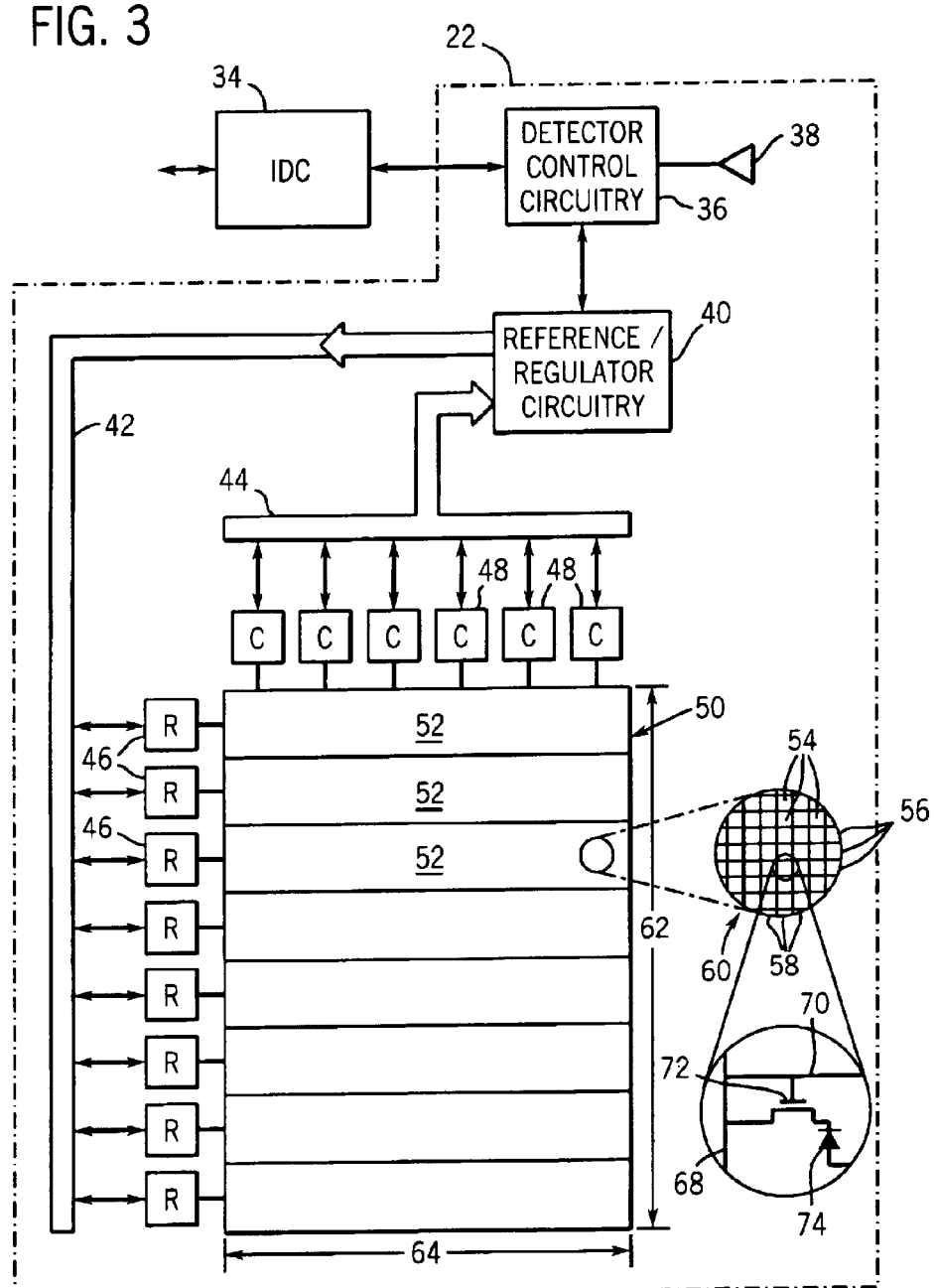
FIG. 3 is a diagrammatical representation of certain of the functional circuitry for producing image data in a detector of the system of FIG. 1.

FIG. 3 is a diagrammatical representation of functional components of an exemplary digital detector 22. FIG. 3 also represents an imaging detector controller or IDC 34 which will typically be configured within detector controller 26. IDC 34 includes a CPU or digital signal processor, as well as memory circuits for commanding acquisition of sensed signals from the detector. IDC 34 is coupled via two-way fiber optic conductors to detector control circuitry 36 within detector 22. IDC 34 thereby exchanges command signals for image data within the detector during operation.

Detector control circuitry 36 receives DC power from a power source, represented generally at reference numeral 38. Detector control circuitry 36 is configured to originate timing and control commands for row and column drivers used to transmit signals during data acquisition phases of operation of the system. Circuitry 36 therefore transmits power and control signals to reference/regulator circuitry 40 and receives digital image pixel data from circuitry 40.

In the exemplary embodiment illustrated, detector 22 includes a scintillator that converts x-ray photons received on the detector surface during examinations to lower energy (light) photons. An array of photodetectors then converts the light photons to electrical signals which are representative of the number of photons or the intensity of radiation impacting individual pixel regions of the detector surface. Readout electronics convert the resulting analog signals to digital values that can be processed, stored, and displayed, such as in a display 30 or a workstation 32, following reconstruction of the image. In a present form, the array of photodetectors is formed on a single base of amorphous silicon. The array elements are organized in rows and columns, with each element consisting of a photodiode and a thin film transistor. The cathode of each diode is connected to the source of the transistor, and the anodes of all diodes are connected to a negative bias voltage. The gates of the transistors in each row are connected together and the row electrodes are connected to the scanning electronics. The drains of the transistors in a column are connected together and an electrode of each column is connected to readout electronics.

In the embodiment illustrated in FIG. 3, by way of example, a row bus 42 includes a plurality of conductors for enabling readout from various columns of the detector, as well as for disabling rows and applying a charge compensation voltage to selected rows, where desired. A column bus 44 includes additional conductors for commanding readout from the columns while the rows are sequentially enabled. Row bus 42 is coupled to a series of row drivers 46, each of which commands enabling of a series of rows in the detector. Similarly, readout electronics 48 are coupled to column bus 44 for commanding readout of all columns of the detector.

In the illustrated embodiment, row drivers 46 and readout electronics 48 are coupled to a detector panel 50 which may be subdivided into a plurality of sections 52. Each section 52 is coupled to one of the row drivers 46 and includes a number of rows. Similarly, each column driver 48 is coupled to a series of columns. The photodiode and thin film transistor arrangement mentioned above thereby define a series of pixels or discrete picture elements 54 which are arranged in rows 56 and columns 58. The rows and columns define an image matrix 60, having a known height 62 and a known width 64.

As also illustrated in FIG. 3, each pixel 54 is generally defined at a row and column crossing, at which a column electrode 68 crosses a row electrode 70. As mentioned above, a thin film transistor 72 is provided at each crossing location for each pixel, as is a photodiode 74. As each row is enabled by row drivers 46, signals from each photodiode may be accessed via readout electronics 48, and converted to digital signals for subsequent processing and image reconstruction.

Before imaging system 10 may be used to perform examination sequences, system 10 is properly installed and set up to ensure compliance with customer needs, performance requirements, and various regulatory standards. The calibration procedure includes a process for establishing a "home position" for each of the source 12 and detector 22, the home position providing a reference point in the lateral, longitudinal, and vertical directions from which motion of each of the source 12 and detector 22 along the track 31 and traditional axes 27 and 29 can be controlled and/or monitored, in conjunction with position sensor 18 and 19.

Figure 4:
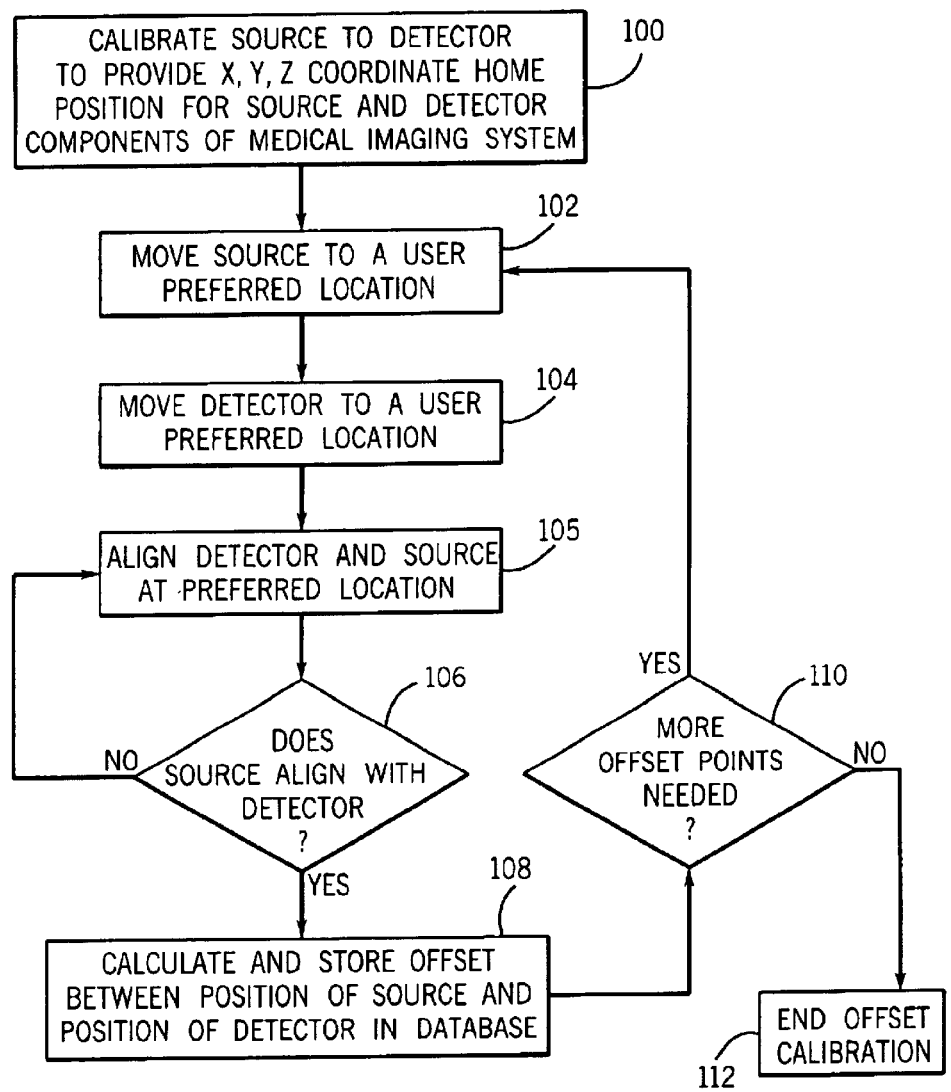
FIG. 4 is flow chart illustrating a positional calibration procedure for the medical imaging system of FIG. 1.

Referring now to FIG. 4, a flow chart for calibrating the medical imaging system 10 is shown. Generally, the calibration comprises a typical source to detector alignment procedure, providing a "home" or reference position. Thereafter, offsets are collected to account for irregularities in the mechanical linkages and/or mounting structures associated with the medical imaging system, as described below.

The home position is determined at a first known source to image distance (SID), typically 100 cm. This initial calibration procedure provides the controller 28 with at least a lateral center and a vertical center calibration point for the detector 22. The vertical and lateral center points are used in conjunction with feedback signals from the position sensor 18 associated with source 12 and the position sensor 19 associated with detector 22 to center the x-ray beam 16 at the center of the detector 22 during operation. After the initial calibration is complete, the distance between the source 12 and detector 22 is changed, and the height of the detector 22 may also be changed. At the second position, if the source 12 and detector 22 are misaligned, an offset is determined.

The offset, as described below, is shown to be in the vertical direction, however, latitudinal and longitudinal offsets can also be determined. The procedure can be provided at a number of varying locations, and offsets in one or more of the latitudinal, longitudinal, and vertical directions stored in a database. The stored offsets can thereafter be retrieved to correct the position of the source 12 and/or detector 22 by activating the motor controller 26 to drive the selected component to the location specified by the offset in real time, as described more fully below.

Referring again to FIG. 4, a flow chart illustrating the steps in the positional calibration process is shown. The steps as described are with reference to a medical imaging system 10 comprising a source 12 coupled to an overhead tube structure (OTS) mounted on a rail system 31, as shown in FIG. 1, and a detector 22 provided on an upright vertical positioner or wall stand 25, also as described above. However, it will be apparent that the method described can also be applied for use with a medical imaging system 10 including a source 12 and a detector 22 mounted to a horizontal positioner 23, or for a system including both a vertical 25 and horizontal 23 positioner, or various other multi-axes positioners.

Figure 5:
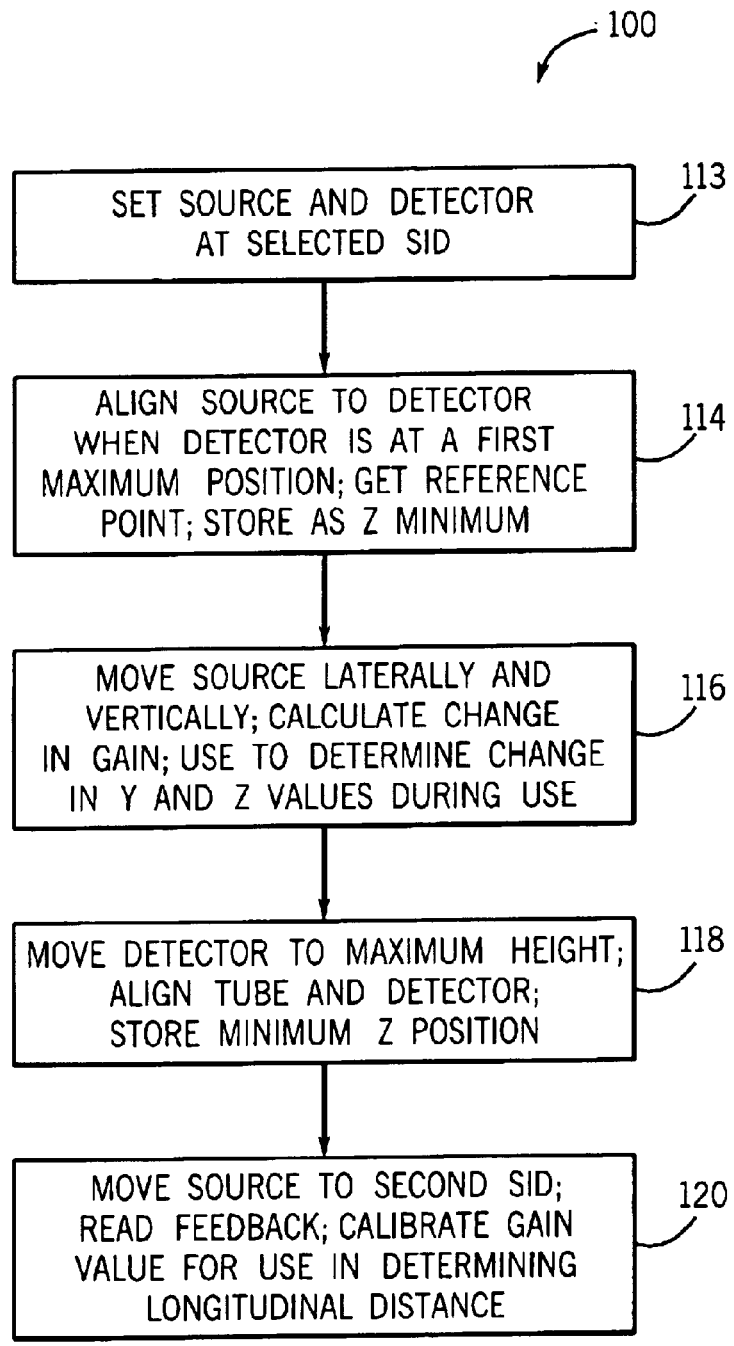
FIG. 5 is a diagrammatic block diagram of an exemplary initial calibration process for calibrating the position of the medical imaging system of FIG. 1.

Referring still to FIG. 4, during installation in step 100, the medical system 10 is initially calibrated to provide a "home position" or reference point for the source 12 and detector 22, defining a zero point for each of the longitudinal, lateral, and vertical positions (Cartesian x, y, and z) from which movement of both the source 12 and detector 22 can thereafter be controlled and monitored during operation, the source 12 being monitored with reference to position sensor 18 and the detector 22 with reference to position sensor 19. Referring now to FIG. 5, an exemplary method for determining a home position of step 100 is shown. Here, in step 113 the detector 22 and source 12 are positioned a given distance apart, typically a source to image distance (SID) of 100 cm. When the source 12 and detector 22 are properly positioned, the detector 22 is moved along translational axis 27 to a maximum position, and the source 12 is aligned with the detector 22 using, for example, the laser beam 17 (step 114). When aligned the position data acquired from each of the position sensors 18 and 19 is stored, providing a vertical maximum for each of the source 12 and detector 22. Next (step 116), the source 12 is activated and moved vertically and latitudinally across the detector 22. Feedback from the detector control circuit 36 of detector 22 is stored and a gain is determined providing information relating the latitudinal and vertical position of the sensor 12 to the detector 22, e.g. in the Cartesian y and z directions. Next (step 118), the detector 22 is moved along translational axis 27 to the minimum height position, and the source 12 is again aligned with the detector, as described above. Positional data from position sensors 18 and 19 is again stored, providing a vertical or z maximum coordinate. After these positions are recorded the SID is changed (step 120), the source 12 being, for example, moved closer to the detector 22 to a distance of typically 65 cm. At this point, the source 12 is again activated and feedback from the detector 22 is read to determine a gain value which provides information relating to the relative position of the source 12 and detector 22 in the longitudinal or x direction. At the completion of this process, a home x, y, and z position for each of the source 12 and detector 22 is determined. While a specific method has been described, a number of methods are known for calibrating a home position, and a number of different calibration procedures could be used to establish this point.

Figure 6:
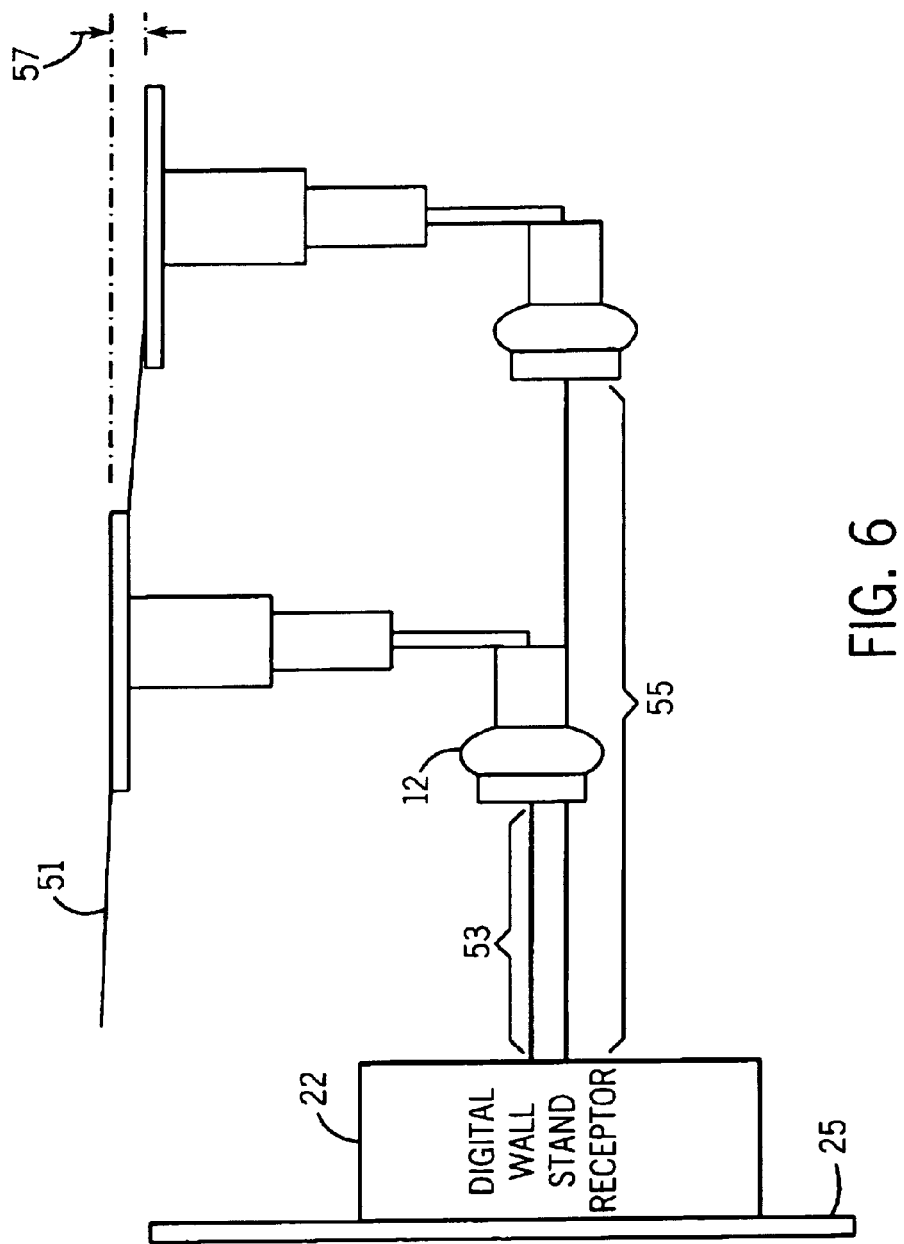
FIG. 6 is an elevational view of the source and detector of FIG. 1, illustrating an offset induced by structural irregularities in the medical imaging mounting system, and a corresponding induced offset.

At the completion of this process, a latitudinal, longitudinal, and vertical home position is established and stored in the controller 28. As the source 12 and detector 22 are moved away from the home position, the controller 28 should align the source to the detector 22 irrespective of the relative positions of these devices. However, due to mechanical misalignments in the rails, translational axes, or other components of the system, and further due to variations in the walls, ceilings, and or floor heights of the examination room, offsets can be introduced. Referring now to FIG. 6, a typical example of this problem is shown. Here the source 12 is mounted to a ceiling 51 of the examination room. The height of the ceiling changes between the first, home position at SID 53, and a second selected SID 55, thereby causing a misalignment between the source 12 and detector 22, here a vertical offset 57. The misalignment of the x-ray beam 16 on the source 22 can result to inaccuracies in the image such as cropping of the image, which can hamper the efficiency and accuracy of a medical examination.

Referring again to FIG. 4, after the home position is determined in step 100, therefore, additional data is acquired to provide offset information to correct for misalignment of the source 12 and detector 22 at various locations. To obtain the offset information in step 102, the operator or field engineer moves the source 12 to a selected SID preferred by the user. The field engineer can also optionally adjust the height of the detector 22 along the translational axes 27 to a height preferred by the user (step 104). When the components are properly positioned, the operator or field engineer activates the laser 23 and aligns the source 12 to the detector 22 (step 105). The field engineer then checks to determine whether the laser beam 17 is centered on the detector 22 (step 106). If the source 12 and the detector 22 are aligned, the field engineer activates a complete button on the user interface of the workstation 32. Upon receipt of a complete signal, the controller 28 reads the position data from the position sensor 18, compares the position to an expected position, calculates an offset between the position of the source 12 and the detector 22 and stores this offset in a database which can include, for example, a lookup table of offset data (step 108).

Once the source 12 and detector 22 are aligned at the alternate SID, no additional steps are required to determine an offset at the user preferred location. It may be desirable, however, to provide additional offset data points. Therefore, the operator makes a determination whether it is desirable or necessary to test the alignment at additional SID distances (step 110). If more points are required, the operator returns to step 102, again moves the source 12 to a different SID and repeats the steps provided above. If not, the procedure is ended (step 112).

As noted above, the offsets can be stored in a look-up table, wherein the offset is treated as a function of the selected SID during operation. Therefore, during real-time medical imaging, the controller 28 refers to the lookup table (LUT) and retrieves offset data as follows:

$$\text{offset} = LUT(SID)$$

The offset value is used by the controller 28 to drive the motor controller 26 to provide a physical offset of the source 12 as follows:

$$OTS\_Vertical\_Height = OTS\_Actual\_Feedback + \text{offset}(SID)$$

After the offset positions are determined, furthermore, appropriate offsets to be applied between known SID locations can be found using, for example, linear interpolation techniques. Other mathematical methods for estimating the actual aligned position for the source 12 to the detector 22, including polynomial equations, neural network technology, and other methods which predict or calculate an output based on known offset data can also be used.

The approach has been described with reference to determining a vertical offset,. However, this approach can be extended to correct for inaccuracies of the x-ray room structure in the lateral and longitudinal directions as well, providing information related to structural inaccuracies both relative to the installed x-ray system and the examination room or superstructure. Based on offset measurements in all directions (vertical, longitudinal and lateral), a 3-D "map" of offset corrections can be provided to compensate for structural or installation inaccuracies. The offsets provided in the 3D map can be stored, as discussed with respect to the look-up table above, as a function of the relative location of the source 12 and detector 22, and used during real time to correct for variations. Furthermore, in a medical imaging system 10 which provides non-perpendicular tracking of the source 12 and detector 22, a 3-D offset map for various source and/or detector angles can be provided.

Although a specific method for determining an alignment offset has been shown using a calibration procedure, a number of variations are available, and the invention is not intended to be limited to this method. In another approach, for example, x-ray image feedback data acquired from the detector 22 during operation of the medical imaging system 10 is used by the controller 28 to calculate and compensate the source 12 to detector 22 alignment during real time for operation. For example, a uncollimated calibrating field of view of 5 cm×5 cm can be used. After an exposure is acquired, the entire detector area is read out to form an image. The uncollimated area of 5 cm×5 cm will be seen on the image, and an automated method can be used to detect the center of the 5 cm×5 cm field of view. The offset of this center from the center of the entire image can be used to calculate an offset between the position of the source 12 and the detector 22. The procedure may be repeated for various SIDs to, again, from a look-up table. An approach employing feedback from the detector can be fully automated with no user interaction.

Furthermore, while the present method has been discussed with reference to structural irregularities in the mechanical linkages and examination room or superstructure, the present invention may also be applied to correct for changes or variations in the mechanical tolerances of the system induced through use of the medical imaging system. Normal use of the system can result in "drift", resulting in incorrect positioner feedback, or variations in the output of the electrical feedback sensors and measuring circuits, further adding to the mechanical error. Variations such as these can be accounted for by re-calibrating the system, as described above, at the initial reference point (say 100 cm). An offset for this point can be stored and the remainder of the database of offsets can be adjusted by this constant.

An alternate means for compensating for this mechanical and electrical drift as well as fine tuning the initial 3-D offset map, would be to use "image offset from center data" after each collimated exposure during normal usage to adjust the offset parameters for the corresponding spatial coordinates. Appropriate filtering could be added to ensure a low bandwidth on the adjustment. Smaller adjustments in the same direction to adjacent points in the 3-D offset map could also be made as the offset errors would likely be slowly varying as opposed to having discrete steps. This type of real-time correction in conjunction with a digital x-ray detector would enable the offset map to become more accurate with system usage.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method for calibrating the alignment of a source to a detector in a medical imaging system to account for variations due to mechanical or physical misalignments in the system, the method comprising the following steps:

determining a reference position for each of the source and the detector at a known source to image distance;

moving the source to a second source to image distance;

determining an offset between the expected location of the source and the actual location of the source at the second source to image distance;

during operation, moving the source by a distance equivalent to the offset, wherein the source and detector are aligned.

2. The method as defined in claim 1, further comprising the step of adjusting the position of the detector in at least one direction.

3. The method as defined in claim 1, wherein the offset is determined during a calibration process.

4. The method as defined in claim 1, wherein the offset is determined during real time operation of the system.

5. A method for calibrating a source and a detector in a digital radiographic system, the method comprising the following steps:

selecting a first source to image distance;

calibrating an alignment of the source and the detector wherein a reference position in at least one of a longitudinal, latitudinal, and vertical direction is determined for each of the source and the detector;

storing the reference positions;

moving the source to at least a second source to image distance;

determining an offset calculated from the misalignment of the source and the detector at the second location as a function of an expected position of at least one of the source and the detector and an actual position of the at least one of the source and the detector;

storing the offset wherein, during operation, the offset is used to align the source with the detector.

6. The method as defined in claim 5, wherein the source is mounted to a superstructure and the offset is due to a variation in the superstructure surface.

7. The method as defined in claim 5, wherein the detector is mounted to a wall stand.

8. The method as defined in claim 5, wherein the source is mounted to a rail system on a ceiling in an examination room and the offset is due to a variation in the height of the ceiling.

9. The method as defined in claim 5, wherein the offset is calculated during a calibration procedure.

10. The method as defined in claim 5, wherein the offset is calculated during operation of the digital radiographic system.

11. A method for calibrating a digital radiographic imaging system, the method comprising the following steps:

(a) calibrating a home position at a first known source to image distance;

(b) moving the source to a second source to image distance;

(c) directing the source at the detector;

(d) moving the source to an aligned position, wherein the source is aligned with the detector;

(e) calculating an offset as a function of a difference between an expected location of at least one of the source and the detector and the actual location of the at least one of the source and detector the aligned position;

(f) storing the offset; and (g) repeating steps (c) through (f) to develop a map of offsets for the digital radiographic system.

12. The method as defined in claim 11, further comprising the step of correlating the offset to a present location during operation, retrieving the offset, and moving the source to align with the detector at the present location.

13. The method as defined in claim 11, further comprising the steps of:

(g) determining a present source to image distance during operation;

(h) determining a first and a second offset at locations before and after the present source to image distance; and (j) interpolating to obtain an offset at the present source to image distance.

14. The method as defined in claim 11, wherein the offsets are stored as a function of source to image distance.

15. The method as defined in claim 11, wherein the offsets are in at least a vertical direction.

16. The method as defined in claim 11, wherein the offsets are provided in at least one of a longitudinal, latitudinal, and vertical direction.

17. The method as defined in claim 11, wherein the offsets are provided in each of a vertical, longitudinal, and latitudinal direction.

18. The method as defined in claim 11, wherein the offsets are provided in an angular direction.

19. The method as defined in claim 11, wherein the offsets are provided in a rotational direction.

20. The method as defined in claim 11, further comprising the step of periodically re-establishing the offsets to correct for operational-induced offsets.

* * * * *